United States Patent [19]

Melsky et al.

[11] Patent Number: 4,978,338
[45] Date of Patent: Dec. 18, 1990

[54] IMPLANTABLE INFUSION APPARATUS

[75] Inventors: Gerald S. Melsky, Lexington; Frank R. Prosl, Duxbury, both of Mass.

[73] Assignee: Therex Corp., Walpole, Mass.

[21] Appl. No.: 184,244

[22] Filed: Jun. 20, 1988

[51] Int. Cl.⁵ .............................................. A61M 5/00
[52] U.S. Cl. ..................................... 604/93; 604/132; 604/86
[58] Field of Search ................. 604/93, 175, 131, 132, 604/140, 141, 86, 83, 82, 43

[56] References Cited

U.S. PATENT DOCUMENTS

| | | |
|---|---|---|
| 3,552,441 | 1/1971 | Luhleich . |
| 3,730,170 | 5/1973 | Michael . |
| 3,731,681 | 5/1973 | Blackshear et al. . |
| 4,193,397 | 3/1980 | Tucker . |
| 4,258,711 | 3/1981 | Tucker . |
| 4,496,343 | 1/1985 | Prosl . |
| 4,525,165 | 6/1985 | Fischell . |
| 4,692,146 | 9/1987 | Hilger ................................. 604/175 |

*Primary Examiner*—C. Fred Rosenbaum
*Assistant Examiner*—Denise W. DeFranco
*Attorney, Agent, or Firm*—Nutter, McClennen & Fish

[57] ABSTRACT

Implantable infusion apparatus includes a housing with an inlet passage extending into the housing at a pronounced promontory on the housing wall. The passage has an outer end at the top of the promontory and an inner end defined by a needle stop positioned inside the housing. Self-sealing septa mounted in the passage at selected spacings from the needle stop divide the passage into a plurality of aligned inlet ports each of which has its own fluid outlet. One of the outlets leads to a pumpable infusate reservoir having an outlet conduit connected to a catheter that extends outside the housing; another leads directly to the outlet conduit so that while a first fluid is being pumped from the reservoir to the catheter, a second fluid can be introduced into the other inlet port for mixing with the first fluid flowing to the catheter. Several different infusate flow configurations are also disclosed.

45 Claims, 2 Drawing Sheets

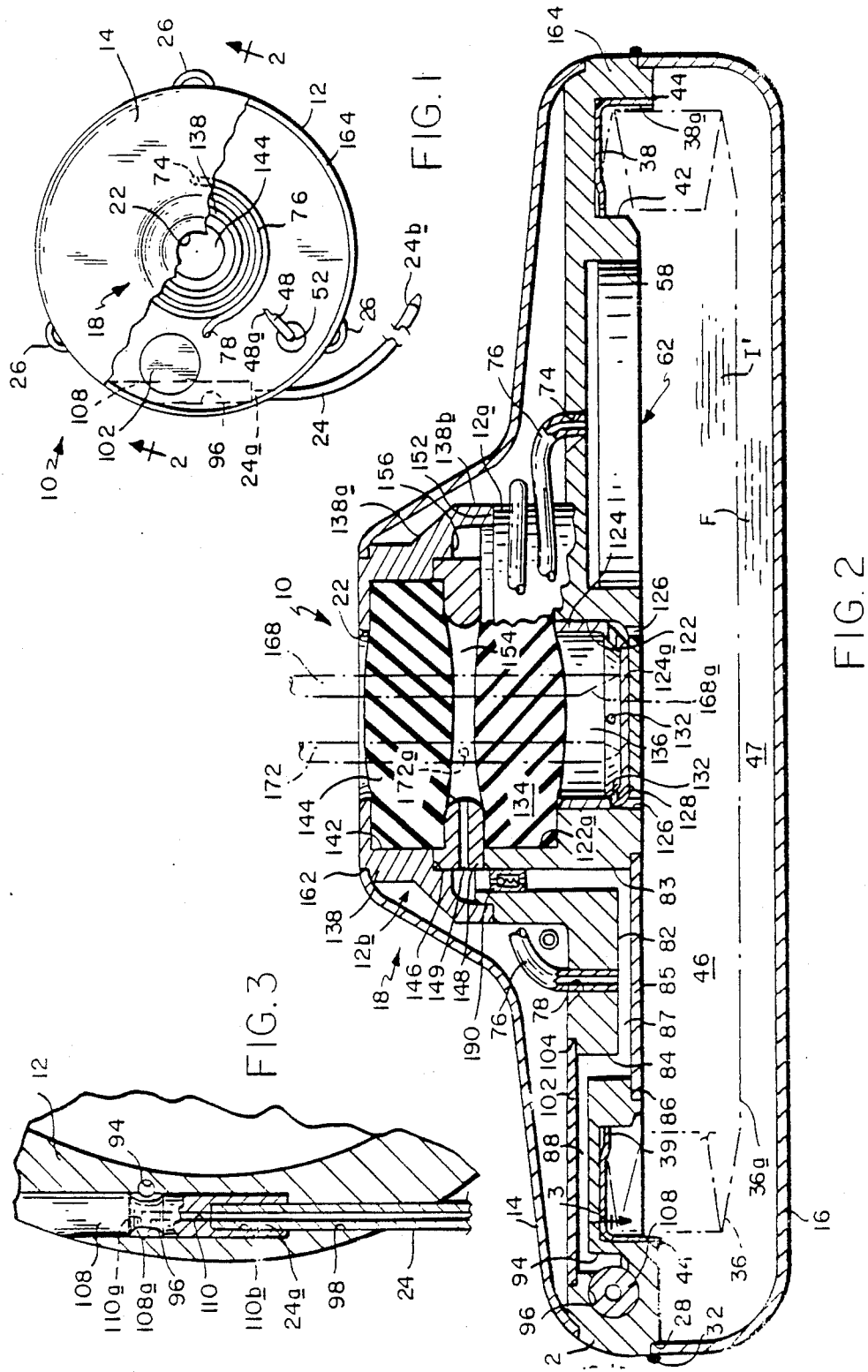

IMPLANTABLE INFUSION APPARATUS

This invention relates to implantable infusion apparatus. It relates more particularly to an implantable self-powered infusate pump which is capable of dispensing a measured dose of infusate to a patient over the long term and which is refillable and rechargeable by trancutaneous injection.

BACKGROUND OF THE INVENTION

Implantable infusion apparatus of the general type with which we are concerned has been in use for a number of years to treat diabetes, Alzheimer's disease, certain types of cancer and other chronic diseases. Basically, the apparatus includes a housing which contains a collapsible infusate reservoir. An inlet port through a wall of the housing communicates with the interior of the reservoir and that passage is closed by a needle-penetrable septum mounted in the housing wall. An outlet passage from the reservoir containing a flow restrictor extends to the housing exterior where it is connected to the proximal end of a flexible catheter.

In use, the apparatus is implanted at a selected location in the body so that the inlet septum is situated directly underneath the patient's skin and the distal end of the catheter is positioned at a selected infusion site. Infusate is delivered to the infusion site by forcing that fluid from the apparatus reservoir through the catheter to the infusion site. The flow restrictor in the reservoir outlet determines the flow rate from the reservoir. When the infusate reservoir becomes empty, it may be refilled by injecting fresh infusate through the apparatus' inlet septum. As noted previously, the inlet is accessible readily by transcutaneous injection using a hypodermic needle or cannula.

In the infusion apparatus of interest here, infusate is expelled from the reservoir to the infusion site by collapsing the reservoir. This collapsing force is provided by a two-phase fluid which is situated in a fluid-tight space outside the reservoir. The fluid is both a liquid and a vapor at physiological temperatures, e.g. 98.6° F., and it exerts a positive and constant pressure over the full volume change of the reservoir. On the other hand, when the infusate reservoir is expanded upon being refilled with fresh infusate during the refilling process described above, the two-phase fluid is compressed with a portion of it reverting to its liquid phase thereby recharging that vapor pressure power source. The construction and operation of inplantable infusate apparatus and pumps of this general type are described in detail, for example, in U.S. Pat. Nos. 3,731,681 and 3,951,147 and in the article entitled "Liquid Dispensers" by B. M. Wright in the *Quarterly Bulletin and Review*, Vol. 16, No. 3, Sept. 1, 1964 and in the *Journal of Physiology*, Vol. 177, (1965). See also the September 1964 Masters Thesis of P. D. W. Soden to be found at Victoria University of Manchester, England.

While the prior art pumps operate satisfactorily, they are relatively expensive to manufacture and to assemble. Also, they are relatively large. For example, one such pump of which we are aware is in the order of 3.3 inches in diameter, one inch thick and weighs about 220 grams. When that prior prosthesis is implanted in a patient's body, the patient is obviously well aware of its presence and may, as a result, suffer considerable discomfort and anxiety.

Some known implantable pumps are difficult to refill in that it is difficult to locate their septa in order to insert needles into their inlet ports to refill or otherwise service the apparatus. This may be due to a combination of factors, including the use of an inlet septum having a small surface area and the inability to distinguish the septum from the remainder of the implanted apparatus. Even if the spot on the patient's skin directly above the septum is marked by a tattoo when the pump is implanted initially, over the course of time, the relative positions of the mark and the underlying septum may change due to patient movements and weight changes. In those known pumps whose catheters exit the housing close to the septum, a mispositioned needle can actually damage the pump by puncturing the rubber catheter. Such damage would, of course, necessitate surgical removal of the pump.

In this connection, we should mention that when refilling an implanted pump, the normal procedure is to insert a hollow needle into the pump's inlet port and allow any remaining volume of the original infusate in the reservoir served by that inlet port to back-flow out through the needle. Then, a fixed volume of the fresh infusate is injected into the reservoir through the needle, after which the needle is withdrawn. It is apparent, therefore, that each emptying and refilling procedure is a time-consuming process that involves skin penetrations and requires the patient to remain still while the needle fixed to his body introduces and/or removes fluid from the infusion device implanted in his body. In many instances, this procedure is performed in a clinic or physician's office or on a hospital out-patient basis. Therefore, each office visit for servicing the pump can be quite expensive.

Also, some implantable apparatus such as those described in U.S. Pat. Nos. 4,193,397 and 4,258,711 have two-pumping chambers or reservoirs enabling them to dispense two different infusate concentrations or infusates. The two pumping chambers are purged and refilled independently by way of separate inlet ports positioned at different locations on the pump housing, each port having its own needle-penetrable septum located underneath the patient's skin.

Another known implantable infusate dispenser disclosed in U.S. Pat. No. 4,496,343 for example, has, instead of a second pumping chamber, an injection portal on the housing wall. This portal is basically a small chamber with an outlet leading to the catheter and an inlet port closed by a self-sealing septum located underneath the patient's skin. Infusate injected transcutaneously into the portal flows directly to the catheter and, therefore, to the infusion site. In other words, the injection process provides the pumping force to deliver the infusate. Such a device can also be used for blood withdrawal.

It is apparent that the proper servicing and utilization of such dual port devices may require many more skin penetrations than are needed to service a pump with a single inlet port. As noted above, once the device is implanted, the positions of the inlet ports and their septa are more or less fixed with respect to the overlying skin area of the patient. Therefore, over the period of implantation, the patient's skin may be punctured many times at the two septa locations resulting in inconvenience and pain for the patient.

Another disadvantage of the prior plural-port implantable pumps is their propensity for being refilled with the wrong fluid. More particularly, after the device is implanted, as noted above, its position may change somewhat relative to a fixed spot on the patient's skin surface. Also, the septa are quite small and indistinguishable. Therefore, when refilling or purging the implanted device, it is quite easy for a nurse to insert a needle into the wrong inlet port if she is not very careful. In the case of a two chamber insulin pump, for example, this could result in the basal reservoir of the pump being refilled with bolus infusate and the bolus reservoir being charged with lower concentration basal infusate, or it could result in one reservoir of that pump being emptied or filled twice and the other reservoir not being serviced at all.

It would be desirable, therefore, if the number and duration of the transcutaneous injections required to access or to service an implanted pump could be minimized, along with the potential for servicing errors. This would not only reduce the risk of infection to the patient, it would also reduce the incidence of epidermal problems associated with implanted refillable infusate pumps of this type, and it would certainly reduce the physical and emotional stress on a patient required to wear such an implanted device.

SUMMARY OF THE INVENTION

Accordingly, it is an object of the present invention to provide improved implantable, refillable, self-powered infusion apparatus.

Another object of the invention is to provide such apparatus which is smaller and more compact than conventional implantable apparatus of this general type.

A further object of the invention is to provide an implantable, refillable infusion pump which is relatively lightweight.

Still another object is to provide such a pump which is relatively easy to manufacture and to assemble as compared to existing devices of this general type.

Yet another object of the invention is to provide an implantable, refillable infusion pump whose refill port or ports can be located easily after the pump is implanted in the patient's body.

A further object of the invention is to provide an implantable, refillable, dual-port infusion device which minimizes the number and duration of skin penetrations required to properly service the device by transcutaneous injection into the device.

Another object of the invention is to provide an implantable, refillable, dual-port infusion apparatus whose inlet ports can be accessed simultaneously with a single penetration of the patient's skin.

Still another object is to provide a dual-port, refillable infusion device which prevents a surgeon or physician from accessing the wrong inlet port when servicing the device after it is implanted.

Still another object is to provide such an infusion device which has sealing redundancy to prevent leakage of infusate within the patient.

Another object of the invention is to provide a device of the type which has a smoothly rounded outer surface which minimizes dead spaces in the implantation area at which infection can occur.

Still another object is to provide an implantable infusion device which has a minimum number of separate tubes and plumbing joints.

Other objects will be, in part, be obvious and will, in part, appear hereinafter.

The invention accordingly comprises the features of construction, combination of elements and arrangement of parts which will be exemplified in the following detailed description, and the scope of the invention will be indicated in the claims.

In general, our infusion apparatus operates on the same basic principles as the implantable infusion pump described in the aforementioned U.S. Pat. No. 3,731,681. Our apparatus can also deliver at least two different infusates to the same infusion site or to different sites in the body of the patient in which the apparatus is implanted. In this, it is similar to the device described in the above-mentioned U.S. Pat. No. 4,496,343. However, our apparatus is constructed in such a way as to materially reduce the overall size and weight of the apparatus as compared to those prior implantable pumps, and additionally, to minimize discomfort and danger to the patient in which the device is implanted by reducing the number of skin penetrations required to service the apparatus after it is implanted, by reducing the incidence of errors in accessing the apparatus and by minimizing patient trauma caused generally by the implantation of the device.

Our infusion apparatus is generally cylindrical having the overall shape of a large pocketwatch. All of the major components and fluid pathways of the apparatus are incorporated in or mounted to a single rigid discoid header or manifold structure. Upper and lower shells mounted to the top and bottom of the header structure are shaped to define internal spaces which enclose various apparatus parts and to give the apparatus a smooth, uninterrupted, gently contoured exterior shape or profile.

A collapsible bellows capsule is positioned in the space between the header and the lower shell. One end of the bellows capsule is open and specially secured in an annular groove present in the underside of the header to facilitate assembly of the capsule as will be described in more detail later. The opposite end of the bellows capsule is closed so that the capsule separates the space between the header and the lower shell into two fluid-tight variable volume compartments. One of these compartments, say, the one inside the capsule, constitutes an infusate reservoir; the other compartment, i.e. the one between the capsule and the lower shell normally contains a two-phase fluid which, at physiological temperatures, produces sufficient vapor pressure to collapse the bellows capsule as described in the above-identified prior art.

When the bellows capsule is collapsed by the driving fluid, infusate inside the capsule flows along a fluid pathway provided in the header to the periphery of the apparatus. That fluid pathway includes an outlet filter recessed into the underside of the header and a flow restrictor to maintain a constant fluid flow from the capsule. Provision is made at the periphery of the apparatus for connecting the proximal end of a flexible catheter so that the catheter lumen is in fluid communication with the fluid pathway in the header. The connection is removed from the surface of the device that faces the skin and is arranged so that the catheter extends tangentially from the apparatus shell so that the catheter will not be punctured when the apparatus is being serviced.

The bellows capsule is located eccentric to the outer diameter of the header thereby providing room on one side of the periphery of the device where the catheter may be connected while keeping the header diameter as small as possible. The catheter may be of any selected length so that when the apparatus is implanted in a patient, it will conduct infusate from the apparatus to a selected infusion site in the patient's body. As will be described in greater detail later, the fluid pathways in the header that conduct infusate from the bellows capsule through the filter and flow restrictor to the catheter can all be formed by simple drilling and/or surface milling operations so that precise manufacturing and defect-free assembly of the apparatus are facilitated.

The present apparatus also includes at least two inlet or access ports by which two different infusates or liquids may be introduced into the apparatus after it is implanted. One of these inlet ports leads to the interior of the bellows capsule, the other inlet port is connected by a passage in the apparatus header to the outlet from the bellows capsule that leads to the catheter. As with prior implantable pumps of the dual-port type, each of the inlet ports is closed by a needle-penetrable, self-sealing septum, which when the pump is implanted in the body, is accessible by transcutaneous injection. Thus, one infusate can be injected into the one inlet port to refill the bellows capsule and to recharge the pump and a second or different infusate may be injected into the other inlet port from which it will flow directly to the catheter so as to supplement the infusate flow thereto from the bellows capsule.

However, whereas prior dual-access devices of this general type have their two inlet ports located at two different locations on the pump housing, in the present apparatus, the two ports are stacked one on top of the other at a pronounced promontory or mesa that projects up at the center of the apparatus. The two ports are isolated from one another and from the outside environment by a pair of septa spaced one on top of the other in a passage that extends down through the header, the inner end of the passage being closed by a permeable needle stop. Thus, the passage segment between the needle stop and the inner septum constitutes the one inlet port which leads to the interior of the bellows capsule and the passage segment between the two septa constitutes the other inlet port which leads directly to the apparatus outlet and the catheter. Thus, when the apparatus is implanted, both of its inlet ports are located at different levels underneath the very same area of the patient's skin.

It should be appreciated that the locating of the common entrance to the inlet ports at a raised rounded promontory or mesa on the apparatus facilitates servicing same. This is because, after implantation, the physician or surgeon can readily locate that promontory and distinguish it from the apparatus housing generally by feeling or pressing against the patient's skin area overlying the general vicinity of the apparatus. When he finds that promontory, it can serve as a target for the needle or cannula. That, coupled with the fact that septa being penetrated have surface areas about four times larger than those on conventional devices of this type means that the servicing of the apparatus can be carried out expeditiously and with minimum discomfort and inconvenience to the patient.

The apparatus is accessed by different needles or cannulae or, more preferably, by a single needle unit which has two parallel fluid paths or lumens. The lumens have separate inlets which permit fluid to be introduced into or withdrawn from each lumen independently. The lumens also have separate outlets which are located at different elevations on the needle unit, as measured from the unit's tip. Moreover, the spacing of the outlets is related to the spacing of the stacked inlet ports of the infusion apparatus so that when the apparatus is implanted and the needle unit is punctured through the patient's skin into the apparatus through the latter's septa until its tip contacts the needle stop, the outlet of each needle unit lumen will automatically be in fluid communication only with the corresponding inlet port of the implanted prosthesis.

Thus, with a single needle penetration, both ports of the implanted device can be accessed independently at the same time. For example, while the infusate reservoir constituted by the bellows capsule is being emptied or filled by way of the needle unit lumen communicating with the one inlet port, a bolus dose of infusate can be infused into the patient via the other lumen which communicates with the other inlet port. It should be understood, however, that although our apparatus allows simultaneous access to both inlet ports of the implanted device, one does not necessarily have to perform the flow operations simultaneously. The point is that our arrangement reduces the number of skin punctures necessary to service an implanted infusion pump or other such device of the dual-port type. It also reduces the length of time that the patient has to be inconvenienced by needles or cannulae penetrating his epidermis. This should, of course, make the wearing of such an implanted device much more bearable to the patient.

It is also important to note that since the fluid paths through the needle unit are keyed or matched to the inlet ports of the implanted apparatus by the corresponding placements of the respective needle outlets and apparatus inlet ports, there is no possibility of a needle accessing the wrong internal port or chamber of the implanted apparatus.

BRIEF DESCRIPTION OF THE DRAWINGS

For a fuller understanding of the nature and objects of the invention, reference should be had to the following detailed description, taken in connection with the accompanying drawings, in which:

FIG. 1 is a plan view with parts broken away of implantable infusion apparatus incorporating our invention;

FIG. 2 is a vertical sectional view on a much larger scale showing the FIG. 1 apparatus in greater detail;

FIG. 3 is a sectional view taken along line 3—3 of FIG. 2;

DESCRIPTION OF THE PREFERRED EMBODIMENT

Figure 4:
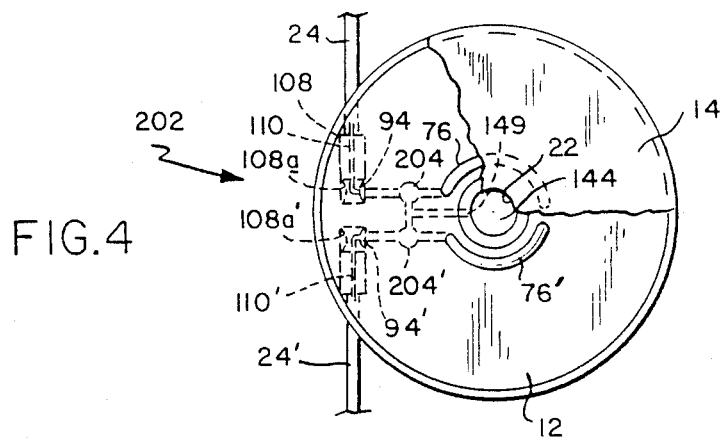
FIG. 4 is a view similar to FIG. 1 of apparatus incorporating our invention which dispenses infusate to two different infusion sites in the body.

Drawing FIG. 1 shows our infusion apparatus generally at 10. The overall size and shape of apparatus 10 are determined by a rigid discoid header or manifold 12, an upper annular shell 14 and a lower cup-like shell 16 (FIG. 2). The shells are secured at their edges to the periphery of the header to form a housing or enclosure which has a more or less continuous, smoothly-contoured outer surface devoid of sharp edges and corners. The header and shells are all made of stainless steel, titanium or other strong biocompatible material. Typically, apparatus 10 has an overall diameter of about three inches and a thickness of about one-half inch except at a central raised mesa or promontory 18 where its thickness is about one inch. The weight of apparatus 10 is only in the order of 120 grams. Actually, apparatus 10 is about one-half as heavy as, and occupies about one-half the volume of, conventional infusion apparatus of this type.

Infusate is introduced into apparatus 10 through an opening 22 at the promontory 18. It leaves the apparatus 10 by way of a flexible catheter 24, the proximal end 24a of which is connected to header 12 at the very edge of the apparatus. In use, apparatus 10 is implanted at a suitable location in the patient's body, e.g. in a subcutaneous pocket in the patient's abdominal wall and it is positioned so that opening 22 is located directly underneath the patient's skin. Small wire loops 26 are welded to the periphery of the header at spaced-apart locations around the apparatus. These can be sutured to body tissue at the implantation site to anchor the apparatus. The distal end 24b of catheter 24 is also sutured in place at a selected infusion site, e.g. a blood vessel or a ventricle space, whose location depends upon the particular patient's physical problem so that the infusate introduced into opening 22 will be conducted via catheter 24 only to that selected site.

Referring now to FIG. 2, the lower edge of header 12 has a circumferential notch 28 that forms a seat for the edge of the lower shell 16 and those two parts are welded all around at 32 so that the header and lower shell together define a fluid-tight space in which is positioned a collapsible bellows capsule 36 preferably of the welded type. The lower end of capsule 36 is closed by an end wall 36a. The upper end of the capsule is open and connected to the underside of header 12.

To effect this connection, a special annular bracket or plate 38 is welded all around at 39 to the inner edge of the uppermost diaphragm 36b of capsule 36 prior to mounting the capsule to the header. The bracket or plate 38 has a slightly larger diameter than that of capsule 36 and its edge margin is bent down to form a peripheral flange 38a that surrounds the uppermost convolutions of the bellows capsule.

The open end of capsule 36, including the bracket 38, seats in a circular groove or channel 42 formed in the underside of header 12 adjacent to the outer edge thereof.

The groove 42 is formed eccentric to the circular perimeter of manifold or header 12 so that capsule 42 is displaced away from the catheter to provide room in the housing for the catheter connection to be described. This keeps the header diameter quite small so that the overall volume of the device is minimized.

Preferably, bracket 38 is shaped so as to space its inner edge, where the weld connection 39 to the bellows is made, from the bottom of the groove 42 to minimize stresses on the weld seam. Groove 42 is deep enough so that when the capsule is fully collapsed, its convolutions nest in groove 42 to a degree that positions the bellows end wall 36a above the lower edge of the bracket flange 38a. This clearance allows a weld bead 44 to be made between that flange edge and the outer edge of the header groove 42 all around the flange without any likelihood of the heat from the welding operation damaging bellows capsule 36. Thus, manufacture of apparatus 10 is facilitated because the bellows capsule can be completely fabricated and attached to bracket 38 outside the apparatus and then the open end of that assembly can be welded to the header reliably all around the bellows capsule at 44 without adversely affecting the bellows capsule. The nesting of the bellows capsule in the header groove 42 also minimizes the compressed volume of the bellows which, in turn, minimizes the bellows extension or stroke required to expel a given volume of infusate from the capsule 36, and thus, the overall thickness of the apparatus.

In the apparatus 10 specifically illustrated herein, the region inside capsule 36 constitutes a reservoir 46 for a first infusate $I_1$. The space or compartment 47 between capsule 36 and shell 16 contains a two-phase fluid F, such as a Freon which is in a two phase state at physiological temperatures with a suitable vapor pressure. Fluid F is introduced into compartment 47 by means of a small tube 48 (FIG. 1) whose lower end is connected to the upper end of a vertical passage 52 in header 12 which leads to that compartment. After that space is charged with fluid F, the upper end of tube 48 is crimped and sealed by a weld 48a. It is important to note that when the apparatus is fully assembled, tube 48 is completely covered and protected by the upper shell 14. However, even if a leak should occur in the tube, the escaping fluid F will be confined in the space under shell 14 and will not be released into the patient.

Still referring to FIG. 2, a shallow generally cylindrical recess 58 is formed in the underside of header 12 at the righthand side thereof, as viewed in that figure. Press fit in that recess is a disk-like filter member 62 consisting of, for example, a 0.2 micron membrane filter.

A small vertical passage 74 is formed in header 12 directly opposite recess 58 for receiving one end of a glass capillary tube 76. The tube end may be anchored and sealed in passage 74 by suitable means such as an epoxy cement. Tube 76 constitutes a fluid flow restrictor and to obtain the necessary degree of restriction for a flow rate of 1 ml/day, for example, the tube must be relatively long. Therefore, the tube is wrapped around a raised header section 12a at the center of the header. The opposite end of tube 76 is received and sealed into a vertical passage 78 extending down through header 12 at a location spaced from passage 74 therein.

A radial groove 82 inscribed in the undersurface of header 12 intercepts the lower end of passage 78. The radially inner end of groove 82 joins the lower end of a vertical passage 83 that extends down from the top of header section 12a. The radially outer end of groove 82, on the other hand, intercepts the lower end of a vertical hole 84 that extends to the upper surface of header 12. Groove 82 is covered by a thin discoid plate 85 seated in a shallow recess 86 provided in the underside of header 12. Thus, a straight fluid conduit (e.g. 0.01×0.05×1.25 inch) exists between passage 83 and hole 84 that functions as a mixing chamber 87 as will be described in detail later.

A similar radial groove 88 is formed in the upper surface of header 12. Groove 88 leads from the upper end of hole 84 to a second hole 94 that extends vertically from the header upper surface part way down through a thickened marginal sector of header 12 where it intercepts a much larger diameter orthogonal passage 96. As best seen in FIG. 3, passage 96 extends horizontally following a chord line through the header that leads into a slightly smaller diameter collinear passage 98, with each passage exiting the header at spaced-apart locations around the perimeter thereof.

Groove 88 is covered by a thin plate 102 which is similar to plate 85 and which seats in a shallow recess 104 in the upper surface of the header. Both plates are held in place by epoxy cement, welding or other suitable means. Thus, a fluid flowing from tube 76 into mixing chamber 87 is conducted via hole 84, groove 88 and hole 94 to passage 96.

Still referring to FIG. 3, passage 96 is arranged to snugly receive a cylindrical plug 108 made of the same material as header 12, the outer end of the plug being flush with the outer surface of the header. Plug 108 is formed with a reduced diameter waist segment 108a which, when the plug has bottomed in its passage 96 as shown in FIG. 3, is situated directly opposite the hole 94 that intercepts passage 96. Plug 108 has an axial passage 110 that extends from the inner end of the plug at least to the plug segment 108a where it joins a short branch passage 110a leading to the surface of plug segment 108a. Further, that plug inner end is counterbored at 110b, the counterbore having the same diameter as passage 98. Both the passage and the counterbore snugly receive the proximal end 24a of catheter 24 which, along with plug 108, is secured and sealed in place by a cement or other suitable means. Thus, the fluid flowing into hole 94 as described above is conducted via plug passages 110 and 110a into the lumen of catheter 24.

It is noteworthy that the catheter 24 exits apparatus 10 well below the rounded edge of the periphery of the upper shell 14 and more or less tangentially. This ensures that there are no sharp bends in the catheter where it leaves the apparatus that could obstruct fluid flow or project into tissue at the implantation site in the patient's body. The catheter is also positioned well away from the upper surface of the apparatus that faces the patient's skin area after the apparatus is implanted. Consequently, there is little likelihood of the catheter being pinched off by tissue ingrowth or being punctured or damaged by an errant needle ostensibly being aimed at opening 22 in order to service the apparatus.

Referring again to FIG. 2, as stated previously, apparatus 10 has a central promontory 18 at the top of the apparatus. This promontory is formed by two header sections and the raised central portion of shell 14. One header section is the aforementioned integral raised section 12a at the center of the header 12. The other is a separate header section 12b that sits on top of section 12a. A relatively large diameter vertical bore or passage 122 is provided in header section 12a for snugly seating a cup-shaped needle stop 124. Bore 122 does not extend to the underside of header 12. However, small holes 126 do pass through the bottom wall of bore 122 to the header undersurface inside capsule 36. Needle stop 124 may be made of metal or, more preferably, of a suitable rigid plastic which does not interact with the infusate in apparatus 10 and which is of a hardness to stop a needle or cannula inserted into passage 122 without unduly damaging the tip of the needle or cannula. The bottom wall 124a of the needle stop is shaped to leave an annular clearance space 128 between the needle stop and holes 126. Also, that wall is provided with a circular array of tiny holes 132 to conduct infusate from passage 122 and the inside of the needle stop to the clearance space 128, whence it will flow through holes 126 into the bellows capsule 36.

Header section 12a also has a counterbore 122a that extends down from the top of that section collinearly with passage 122. Seated in the counterbore is a discoid, needle-penetrable, self-sealing septum 134 made of medical grade rubber or the like. The septum 134 seats snugly in counterbore 122a so that its upper surface is more or less flush with the upper surface of section 12a. Thus, the space inside passage 122 and needle stop 124 below septum 134 constitutes an inlet port 136 for bellows capsule 36, i.e. for infusate reservoir 46 inside the capsule.

The header section 12b that seats on section 12a is a generally cylindrical annular member 138 having an axial bore or passage 142 extending from the underside of that member almost to the top thereof. A smaller diameter bore extends down from the top of member 138 to form the opening 22 at the top of the apparatus that was described at the outset. Typically, that opening is about one-half inch in diameter. A second discoid septum 144 similar to septum 134 is seated in passage 142 so that it completely fills opening 22. Passage 142 is counterbored from below at 146 to receive an annular spacer 148 which engages under septum 144 and holds the septum in place in member 138. Spacer 148 may be made of the same plastic material as needle stop 124 and for reasons to become apparent shortly, a radial hole or passage 149 is provided through that spacer.

As noted previously, header section 12b is designed to seat on header section 12a. Accordingly, it is provided with a shoulder 138a and a cylindrical skirt 138b that extends down and seats in a circumferential notch 152 at the top of section 12a. When the two sections are stacked as shown, the spacer 148 separates the two septa 134 and 144 so that a short, generally cylindrical space exists between the two septa which constitutes the second inlet port 154 of apparatus 10. As shown in FIG. 2, inlet port 154 is located directly over inlet port 136 and both ports are accessible through the single opening 22 at the top of the apparatus.

Also as seen from FIG. 2, the underside of the spacer shoulder 138a is flared so as to leave an annular clearance space 156 between the shoulder and the top of header section 12a which space intercepts both the radial hole 149 in spacer 148 and the passage 83 that extends down through header section 12a to the mixing chamber 87. Accordingly, infusate introduced through opening 22 into inlet port 154 is free to flow directly through passage 83 into mixing chamber 87 where it can mix with the infusate from reservoir 46 that enters that chamber by way of capillary tube 76.

After header section 12b is secured to section 12a by epoxy cement, welding or other suitable means, the upper shell 14 of the apparatus is engaged over the top of the header so that its inner edge seats in a circumferential notch 162 at the top of header section 12b and so that its outer edge rests in a circumferential groove 164 at the upper edge of the header periphery. When that shell is secured in place by welding, epoxy cement or the like, the shell protectively encloses the capillary tube 76 and, as noted above, the fill tube 48. It also gives the upper half of apparatus 10, including its promontory 18, a smooth uninterrupted surface and a gently curved contour. In the same manner, the lower shell 16, connected at its edge to the lower edge of the header periphery by weld 32 as described above, protectively encloses bellows capsule 36 and gives the underside of apparatus 10 a similar smooth, gently curved contour so that when the apparatus is implanted, there will be minimal dead spaces created at the exterior surfaces of the apparatus in which body fluids can collect and create potential sites for infections.

The shells 14 and 16 also have a sealing function. As noted above, shell 14 provides sealing redundancy to prevent fluid F leakage through tube 48 from reaching the patient. Both shells minimize the likelihood of leakage of infusate from the apparatus into the patient after the device has been implanted. That is, the shells are impervious and the welded connections of the shells to the manifold at 32, 162 and 164 are all fluid tight. Therefore, if an infusate leak should develop in the glass tube 76 or in the relatively high pressure bolus flow path, i.e. at plates 102 or header notch 152, the leakage would be contained within the space under shell 14. Similarly, a leak in bellows capsule 36 would only result in infusate flowing into the fluid tight chamber 47. In no event would there be uncontrolled fluid flow from apparatus 10 into the patient at the implantation site.

It is apparent from the above description and from the drawings that all of the vertical fluid pathways in the header 12 consist of vertical holes or passages, e.g. 72, 74, 78, 83, 96, 98 and 122, that can be formed easily and precisely by simple drilling operations. On the other hand, the horizontal pathways through the header are formed by surface grooves and recesses, e.g. 58, 82, 86, 88 and 104, which can be inscribed in the header using standard milling or surface grinding processes. Thus the design lends itself to automated manufacture of the apparatus. Indeed, for some applications, it is even possible to mold header 12 (sans section 12b), with all of its various passages and recesses in a single molding operation.

It is worthy of note also that all of the other apparatus 10 parts, such as bellows capsule 36, filter member 62, the glass capillary tube 76, and cover plates 85 and 102 are all mounted directly to the header 12 at precisely defined locations so that there is no possibility of mispositioning those parts during assembly. This helps to insure that infusion apparatus 10 can be produced in quantity on a reliable basis and with few rejects.

After apparatus 10 is implanted in the body with its opening 22 located directly under the patient's skin and the distal end 24b of catheter 24 positioned at the selected infusion site, the apparatus' infusate reservoir 46 may be filled with infusate by inserting a hollow needle (Huber tip), such as the needle shown in phantom at 168 in FIG. 2, through the patient's skin over opening 22 and through septa 144 and 134, in turn, until the needle tip bottoms against the needle stop 124. The needle is provided with an outlet opening 168a adjacent to the tip so that when the needle bottoms against the needle stop as shown in FIG. 2, the opening 168a is level with inlet port 136. Accordingly, infusate flowed into needle 168 will enter port 136 and flow into capsule 36, i.e. reservoir 46, by way of holes 132 and 126.

During the filling operation, a predetermined volume of infusate is injected under pressure into the bellows capsule. This causes the capsule to extend and, in the process to compress the two-phase fluid F in the compartment 47 inside shell 16 so that that fluid assumes its liquid phase, thereby recharging the apparatus' pumping power source in a manner well known in this art. A similar needle 168 can be used to empty fluid from bellows capsule 36 or to refill the capsule with fresh infusate. At the body temperature of the patient, the two-phase fluid F will exert sufficient vapor pressure to collapse capsule 36, thereby forcing infusate $I_1$ from reservoir 46 through the filter member 62 and capillary tube 76 to mixing chamber 87 and thence to catheter 24 as described above.

In order to access the apparatus' second inlet port 154, a needle shown in phantom at 172 in FIG. 2 is inserted through the patient's skin and through septa 144 and 134 until the tip of that needle bottoms against the needle stop 124. Needle 172 has a side opening 172a that is aligned with inlet port 154 when the needle is fully inserted into the apparatus as shown in FIG. 2. Thus the needle 172 can be used to inject a second infusate $I_2$ into the inlet port 154 whence that liquid will flow directly to mixing chamber 87 where it will mix with the infusate $I_1$ being pumped from capsule 36 so that a selected mixture of infusates $I_1$ and $I_2$ will be delivered to the infusion site by way of catheter 24. Since mixing chamber 87 is downstream from the flow restricting capillary tube 76 and the fluid pathway from the mixing chamber to catheter 24 is comparatively large, there is minimal possibility of the infusate $I_2$ being conveyed back into bellows capsule 36 containing infusate $I_1$.

In some instances, it may be desirable to provide a check valve in the flow path from the second inlet port 154. Such a valve is shown at 190 in FIG. 2. It ensures that if a leak should occur in the inner septum 134, the infusate leaking from reservoir 46 into port 154 would not be able to follow the unrestricted flow path through passages 83, 87, 88, etc. to catheter 24. Such a valve 190, e.g. a conventional spring-loaded ball valve, is arranged to open or unseat under a pressure in port 154 that is greater than the vapor pressure of the fluid in compartment 47. In other words, the valve opens only when infusate is being forceably injected into port 154 via needle 172 under a pressure appreciably greater than that exerted by the two phase fluid in compartment 47. Also, if a leak should develop in the outer septum 144, valve 190 will prevent infusate outflow from passage 83.

In actual practice, the needles 168 and 172 may be separate needles or they may be incorporated into a single needle unit having two flow paths or lumens whose outlet openings are spaced apart on the needle unit so that they open into the inlet ports 136 and 154 respectively, as described above. Thus apparatus 10 can be used, for example, to deliver a basal dose of insulin at a controlled, very low flow rate to a patient, with such basal dose being supplemented from time to time by a bolus dose of infusate injected into inlet port 154. If a dual lumen needle unit is used, liquids may be introduced into or withdrawn from inlet ports 136 and 154 independently and simultaneously after only a single puncture of the patient's skin.

Because opening 22 is quite large and is centered in the raised promontory 18 whose location can be determined readily by pressing against the patient's skin, apparatus 10 can be accessed quite quickly and with minimum discomfort to the patient in whom the apparatus is implanted. Since apparatus 10 controls such access so as to prevent each lumen of the needle unit from conducting liquid into the wrong inlet port of the apparatus, there is little likelihood of the patient being given the wrong medication.

While we have depicted and described in detail infusion apparatus having a single infusate reservoir served by an inlet port 136 and with a second inlet port 154 for conducting a second infusate directly to the same infusion site, it is obvious that the principles disclosed here can be extended to other implantable infusion devices.

Figure 5:
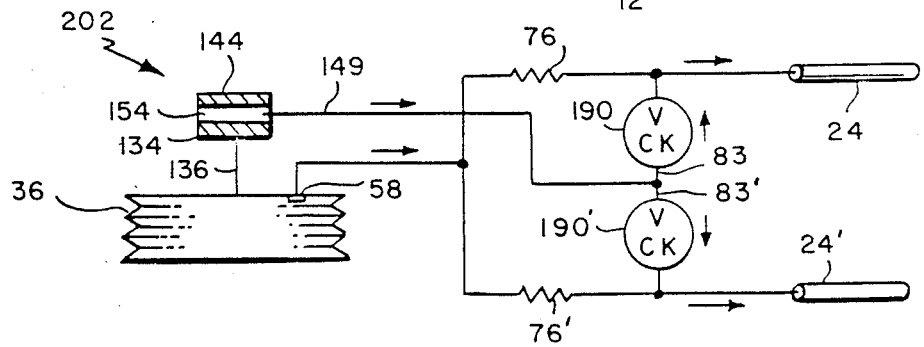
FIG. 5 is a diagrammatic view of the FIG. 4 apparatus.

Our apparatus design also lends itself to the incorporation of a second outlet catheter leading from housing 12. FIGS. 4 and 5 illustrate implantable infusion apparatus 202 which has two outlet catheters 24 and 24' for conducting infusate simultaneously to two different sites in the body, e.g. an artery and a vein. Apparatus 202 is similar to apparatus 10 described above except that it has two capillary tubes 76, 76' leading from filter recess 58 via separate flow paths 204, 204' in manifold 12 to separate vertical holes 94, 94' communicating with two separate passages 110, 110' extending from opposite ends of plug 108 to two different plug waist segments 108a, 108a'. Note that both catheters exit housing 12 tangentially and below the edge of shell 14 for the reasons discussed above.

The outlet passage 149 from the bolus inlet port 154 leads to separate vertical passages 83, 83' in header 12, containing separate check valves 190, 190'. With this arrangement, infusate will flow from capsule 36 to catheters 24 and 24'. Because arterial pressure is higher than venous pressure, the tubes 76, 76' have different high resistance flow restrictions to equalize infusate flow to the artery and vein. These regulated infusate flows may be supplemented when necessary by bolus injections into port 154. The bolus flow to the catheters may also be proportioned by downstream flow restrictors (not shown). The two check valves 190, 190' prevent unwanted blood flow from the artery to the vein due to the blood pressure differential in those blood vessels.

Figure 6:
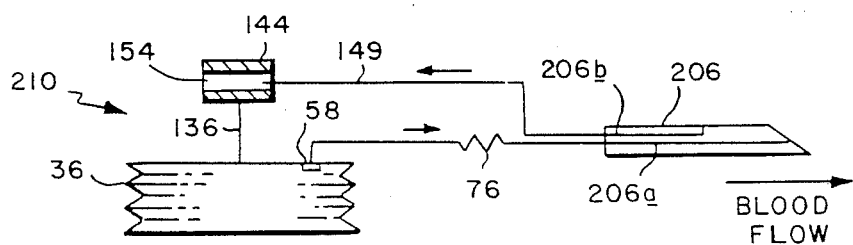
FIG. 6 is a similar view of an apparatus embodiment having a dual lumen outlet catheter.

Apparatus 202 may also be modified easily to have a single dual lumen outlet catheter such as catheter 206 in FIG. 6. In this event, plug 108 would have parallel passages 110 and 110' connecting plug waists 108a, 108a' to the catheter lumens 206a, 206b.

Of course, if in apparatus 202 a bolus capability is needed at only one of the catheters or only one of the catheter lumens, e.g. 24, 206a, the passage 83' and its valve 190' may be eliminated.

FIG. 6 shows an implantable device 210 similar to apparatus 10 but fitted with a single dual lumen catheter 206. When the catheter is placed at a selected infusion site, i.e. a blood vessel, infusate from capsule 37 may be flowed to that vessel through catheter lumen 206a, while at the same time, blood may be withdrawn from the vessel via catheter lumen 206b by a suction needle inserted into inlet port 154. As shown in FIG. 6, the outlets of the two lumens may be spaced apart along the catheter so that the blood is withdrawn from the blood vessel upstream from the infusion site.

A similar arrangement using either a dual lumen catheter or two separate catheters may be used to infuse a patient while having the capability of monitoring the patient's blood pressure. For this, a standing column of saline or other biocompatible liquid is maintained in the fluid path from inlet port 154 to its catheter lumen and a needle-like pressure transducer is inserted into port 154 to transmit the blood pressure variations coupled to it by the liquid column to an external pressure monitor.

This invention can also be incorporated into a dual-chamber pump of the type described in the aforementioned U.S. Pat. No. 4,193,397. In this event, the inlet port 154 would be connected by fluid pathways in the header 12 to a second bellows capsule inside shell 16 constituting the reservoir for a second infusate. Indeed, implantable pumping or portal apparatus may be provided with three or more inlet ports stacked in the manner described, with those ports being accessed independently by a needle unit having a corresponding number of flow paths or lumens, each one of which opens into a different one of the inlet ports.

It will thus be seen that the objects set forth above, among those made apparent from the preceding description, are efficiently attained, and since certain changes may be made in the above constructions without departing from the scope of the invention, it is intended that all matter contained in the above description or shown in the accompanying drawings be interpreted as illustrative and not in a limiting sense.

What is claimed as new and desired to be secured by Letters Patent of the United States is:

1. Implantable infusion apparatus comprising
   a hermetically sealed housing, said housing including a pronounced outwardly projecting promontory positioned at or near the center of the housing away from the periphery thereof;
   a passage into said housing at said promontory;
   needle stop means at the end of said passage inside said housing;
   a first needle-penetrable, self-sealing septum mounted in said passage at a selected spacing from said needle stop means, said first septum being located at the outer surface of said housing at the top of said promontory;
   a second septum mounted in said passage at a selected spacing from said first septum thereby to divide said passage into a first segment extending between said needle stop means and said first septum and a second aligned segment extending between said first septum and said second septum;
   first and second fluid outlets from said first and second passage segments;
   a pumpable infusate reservoir inside said housing in fluid communication with one of said fluid outlets, the other of said fluid outlets being in fluid communication with fluid flow means extending within said housing;
   a catheter extending from the housing for conducting fluid from said apparatus to an infusion site; and
   a conduit in said housing for conducting fluid from said reservoir to said catheter.

2. The apparatus defined in claim 1 wherein the other of said fluid outlets is also in fluid communication with said catheter.

3. The apparatus defined in claim 2 wherein
   A. said catheter is a dual lumen catheter;
   B. said conduit is in fluid communication with one lumen of said catheter; and
   C. said other of said outlets conducts fluid to the other lumen of said catheter.

4. The infusion apparatus defined in claim 2 wherein said conduit from said reservoir to said catheter includes a filter and a fluid flow restrictor.

5. The infusion apparatus defined in claim 4 wherein the flow restrictor comprises a length of glass capillary tubing.

6. The infusion apparatus defined in claim 4 wherein
   A. said conduit also includes a mixing chamber downstream from said flow restrictor; and
   B. the other of said fluid outlets leads to said mixing chamber, so that while a first fluid is being expelled from said pumpable reservoir to said mixing chamber, a second fluid introduced into said second passage segment will flow to and be mixed in said mixing chamber with said first fluid so that a fluid mixture will be conducted to the catheter.

7. The apparatus defined in claim 7 wherein said pumpable infusate reservoir includes
   A. a collapsible infusate chamber; and
   B. means for collapsing the chamber to force infusate from the chamber through said conduit to said catheter.

8. The apparatus defined in claim 7 wherein the collapsing means comprise a two-phase fluid confined inside said housing adjacent to said chamber, said fluid exerting sufficient vapor pressure at physiological temperatures to collapse said chamber.

9. The apparatus defined in claim 1 wherein said housing is generally circular and said catheter exits said housing substantially tangentially.

10. The apparatus defined in claim 1 and further including
A. a second catheter, said second catheter exiting said housing substantially tangentially and collinearly to said catheter; and
B. means for conducting fluid from the other of said fluid outlets to said second catheter.

11. The apparatus defined in claim 1 wherein said pumpable infusate reservoir comprises
A. rigid manifold means inside the housing;
B. a collapsible metal bellows capsule having an open end mounted to the manifold means, the opposite end of the capsule being closed; and
C. means in the housing for collapsing the bellows capsule.

12. The apparatus defined in claim 1 wherein
A. said passage, said outlets and at least a portion of said conduit are formed in said manifold means; and
B. said needle stop, septa and catheter are all mounted to said manifold means adjacent to the open end of said bellows capsule.

13. The apparatus defined in claim 12 wherein the open end of the bellows capsule is recessed into a circular groove with an open edge formed in said manifold means.

14. Implantable infusion apparatus comprising:
a hermetically sealed housing;
a passage into said housing;
needle stop means at the end of said passage inside said housing;
a first needle-penetrable, self-sealing septum mounted in said passage at a selected spacing from said needle stop means;
a second septum mounted in said passage at a selected spacing from said first septum thereby to divide said passage into a first segment extending between said needle stop means and said first septum and a second aligned segment extending between said first septum and said second septum;
first and second fluid outlets from said first and second passage segments;
a pumpable infusate reservoir inside said housing in fluid communication with one of said fluid outlets, said reservoir including rigid manifold means inside the housing, means defining a circular groove with an open edge in said manifold means, a collapsible metal bellows capsule having an open end recessed into said groove, the opposite end of said capsule being closed, and means for mounting said bellows open end to said manifold means, said mounting means comprising a
bracket including an annular body having an inner edge seated in said groove and a cylindrical flange having a free edge extending from the periphery of said body to the open edge of said groove,
the inner edge of said body being connected by a continuous weld to the open end of said bellows capsule and
the free edge of said flange being connected by a continuous weld to said open edge of said groove in the manifold means,
means in said housing for collapsing the bellows capsule;
a catheter extending from the housing for conducting fluid from said apparatus to an infusion site, and
a conduit in said housing for conducting fluid from said reservoir to said catheter, said passage, said outlets and at least a portion of said conduit being formed in said manifold means, and said needle stop, septa and catheter all being mounted to said manifold means adjacent to the open end of said bellows capsule.

15. Implantable infusion apparatus comprising:
a hermetically sealed housing;
a passage into said housing;
needle stop means at the end of said passage inside said housing;
a first needle-penetrable, self-sealing septum mounted in said passage at a selected spacing from said needle stop means;
a second septum mounted in said passage at a selected spacing from said first septum thereby to divide said passage into a first segment extending between said needle stop means and said first septum and a second aligned segment extending between said first septum and said second septum;
first and second fluid outlets from said first and second passage segments;
a pumpable infusate reservoir inside said housing in fluid communication with one of said fluid outlets, said reservoir including rigid manifold means inside the housing, means defining a circular groove with one open edge in said manifold means, a collapsible metal bellows capsule having an open end recessed into said groove, the opposite end of the capsule being closed, and means for mounting said bellows open end to said manifold means at said groove;
means in the housing for collapsing the bellows capsule;
a catheter extending from the housing for conducting fluid from said apparatus to an infusion site,
said manifold means being disk-shaped and
said circular groove being located eccentric to the circular periphery of said manifold means so that the groove is displaced away from said catheter,
and a conduit in said housing for conducting fluid from said reservoir to said catheter, said passage, said outlets and at least a portion of said conduit being formed in said manifold means and said needle stop, septa and catheter all being mounted to said manifold means adjacent to the open end of said bellows capsule.

16. The apparatus defined in claim 1 and further including flow check means for preventing fluid flow from said other of said fluid outlets to said second passage segment.

17. Implantable infusion apparatus comprising:
a rigid discoid header having opposite first and second surfaces;
A circular groove in said header second surface;
a collapsible bellows capsule having a closed end and an open end;
mounting means for mounting said bellows open end to said header second surface, said mounting means including an annular bracket having a peripheral flange and radially inner and outer edges, the inner edge of said bracket being connected along its entire circular length to the capsule open end, said bracket and said capsule open end being seated in said groove so that said flange extends adjacent to the radially outer wall of said groove and connecting means connecting said bracket outer edge along its entire circular length to said header all around said groove;

a first passage in said header extending between said header surfaces opposite the bellows capsule;

a second passage extending into said header from the periphery thereof;

a liquid conduit extending from said first passage to said second passage;

a self-sealing inlet port in said header opposite the bellows capsule, said inlet port being accessible from said header first surface, and fluid conduit means extending between said inlet port and the interior of said capsule.

18. The apparatus defined in claim 17 wherein said capsule is made of a biocompatible metal and said connections are welds.

19. The apparatus defined in claim 17 wherein said liquid conduit includes a length of flow-restricting glass tubing.

20. The apparatus defined in claim 17
 A. wherein said second passage extends along a chord of said header; and
 B. further including a flexible catheter having one end secured in a fluid-tight manner in said passage so that the catheter extends from the periphery of the apparatus more or less tangentially.

21. The apparatus defined in claim 17 wherein
 A. said header includes a central mesa at said header first surface, said mesa having a central perpendicular axis; and
 B. said inlet port is located in said mesa.

22. The apparatus defined in claim 21 further including
 A. a smoothly contoured cup-like first shell mounted to said header second surface at the periphery thereof, said first shell defining with said header a first fluid-tight compartment that contains said capsule; and
 B. a second smoothly contoured annular shell mounted to said header first surface, said second shell covering said second surface except at said inlet port and defining with said header a second fluid-tight compartment that overlies said first and second passages and said conduit.

23. The apparatus defined in claim 22 wherein said liquid conduit includes a length of flow restricting glass tubing wound around said mesa in said second compartment.

24. The apparatus defined in claim 23 wherein
 A. said liquid conduit also includes a third passage in said header extending between said second passage and a location at said header first surface in said second compartment; and
 B. said tubing is connected between said first and said third passages.

25. The apparatus defined claim 22
 A. wherein said second passage extends along a chord of said header spaced from the outer edge of said second shell and has opposite ends spaced apart on the header periphery; and
 B. further including a first catheter having one end in fluid-tight communication with one end of said second passage and a second catheter having one end in fluid-tight communication with the other end of said second passage so that said catheters extend more or less tangentially from the apparatus in opposite directions.

26. The apparatus defined in claim 22 and further including
 A. a second self-sealing inlet port in said header, said second port being aligned along said axis in said mesa with said first port; and
 B. liquid conducting means in said header extending from said second inlet port to said liquid conduit.

27. The apparatus defined in claim 26 wherein
 A. said conduit includes a liquid flow restriction; and
 B. said conducting means join said liquid conduit downstream from said flow restriction.

28. The apparatus defined in claim 27 and further including a check valve in said conducting means to prevent back flow into said second inlet port.

29. The apparatus defined in claim 26 and further including a check valve in said conducting means to prevent back flow into said second inlet port.

30. The apparatus defined in claim 22 and further including means accessible at said header second surface for flowing a two-phase fluid that vaporizes at physiological temperatures into said second compartment.

31. The apparatus defined in claim 22 and further including a plurality of suture loops attached to the outside of said header periphery at spaced apart locations therearound.

32. The apparatus defined in claim 17 and further including
 A. a second self-sealing inlet port in said header, said second port being vertically aligned with said first port and accessible from the header second surface;
 B. a liquid passage in said header extending from said second inlet port to the periphery of the header;
 C. a first catheter having one end in fluid tight communication with said second passage at the header periphery; and
 D. a second catheter having one end in fluid tight communication with said liquid passage at the header periphery.

33. The apparatus defined in claim 32 and further including a standing column of a biocompatible liquid filling said second inlet port, said liquid passage and said second catheter for transmitting pressure pulses from the opposite end of said catheter to said second inlet port for sensing by a needle-like pressure transducer inserted into said second inlet port.

34. Implantable infusion apparatus comprising
 a rigid manifold having opposite first and second surfaces and a pronounced outwardly projecting mesa positioned at or near the center of said second surface away from the periphery thereof, said mesa having a central perpendicular axis;
 a collapsible fluid-tight infusate chamber having a closed end and an open end;
 means for mounting the chamber open end in a fluid-tight manner to the manifold first surface opposite said mesa;
 a self-sealing inlet port in said manifold mesa, said inlet port being accessible from the manifold second surface at the top of said mesa; fluid conduit means extending between said inlet port and the interior of said chamber; and
 a first outlet conduit communicating between said manifold first surface inside said chamber and the manifold periphery.

35. Implantable infusion apparatus comprising
a rigid manifold having opposite first and second surfaces and a central mesa at said second surface, said mesa having a central perpendicular axis;
a collapsible fluid-tight infusate chamber having a closed end and an open end;
means for mounting the chamber open end in a fluid-tight manner to the manifold first surface opposite said mesa;
a self-sealing inlet port in said manifold mesa, said inlet port being accessible from the header second surface at the top of said mesa;
fluid conduit means extending between said inlet port and the interior of said chamber;
a first outlet conduit communicating between said manifold first surface inside said chamber and the manifold periphery;
  a second self-sealing inlet port in said manifold mesa, said second inlet port being in alignment along said axis with said first inlet port and accessible from the manifold second surface at the top of said mesa; and
  a second outlet conduit in said manifold communicating between said second inlet port and the periphery of said manifold.

36. The apparatus defined in claim 35 wherein first and second outlet conduits join in said manifold to form a Y-conduit that has a single outlet at the periphery of the manifold and which receives fluid from both said chamber and said second inlet port.

37. The apparatus defined in claim 36 and further including a check valve in said Y-conduit downstream from the joint with said first outlet conduit to prevent fluid back flow into said second inlet port.

38. The apparatus defined in claim 37 and further including a fluid flow restrictor in said Y-conduit upstream from the joint with said second outlet conduit.

39. The apparatus defined in claim 38 wherein said Y-conduit includes
  A. a first manifold passage extending into said chamber;
  B. a second manifold passage extending into the manifold from the periphery thereof; and
  C. a flow-restricting glass capillary tube wound around said mesa and connected between said first and second passages.

40. The apparatus defined in claim 35
  A. wherein first and second outlet conduits have separate outlets located adjacent to the periphery of said manifold; and
  B. further including first and second catheters having corresponding first ends connected to said first and second conduits respectively.

41. The apparatus defined in claim 35 and further including a dual-lumen catheter having a first end connected to the periphery of said manifold, the two lumens of said catheter being in fluid communication with different ones of said outlet conduits.

42. The apparatus defined in claim 35
  A. wherein said first outlet conduit branches to form a Y-conduit that has first and second outlets at spaced-apart locations on the periphery of said manifold; and
  B. further including a pair of catheters having corresponding first ends connected to said header periphery and being in fluid communication with said first and second outlets respectively; a first check valve connected between said second outlet conduit and one branch of said Y-conduit, and a second check valve connected between said second outlet conduit and the other branch of said Y-conduit, both of said valves preventing back flow from the Y-conduit into said second conduit.

43. The apparatus defined in claim 42 and further including a flow restrictor in each branch of said Y-conduit upstream from the said check valve connected thereto.

44. The apparatus defined in claim 42 wherein said catheters are connected to the header so that they extend more or less tangentially from the apparatus.

45. The apparatus defined in claim 33 and further including
  A. a smoothly contoured cup-like first shell mounted to said header first surface at the periphery thereof, said first shell defining with said header a first fluid-tight compartment that contains said infusate chamber; and
  B. a second smoothly contoured annular shell covering said manifold second surface except that the access to said inlet ports, said second shell being connected to said manifold periphery and said mesa so that the second shell defines with said manifold a second fluid-tight compartment that overlies said first and second outlet conduits.

* * * * *